US005624396A

United States Patent [19]
McNamara et al.

[11] Patent Number: 5,624,396
[45] Date of Patent: Apr. 29, 1997

[54] LONGITUDINALLY EXTENDABLE INFUSION DEVICE

[75] Inventors: Thomas O. McNamara, Los Angeles; Blair D. Walker, Long Beach, both of Calif.

[73] Assignee: Micro Therapeutics, Inc., San Clemente, Calif.

[21] Appl. No.: 550,160

[22] Filed: Oct. 30, 1995

[51] Int. Cl.$^6$ .................................................. A61M 11/00
[52] U.S. Cl. ........................... 604/93; 604/164; 604/264; 604/280; 604/282; 604/53
[58] Field of Search .............................. 604/93, 22, 264, 604/266, 269, 280, 281, 282, 170, 164, 53, 51–52, 28

[56] References Cited

U.S. PATENT DOCUMENTS 4,586,923  5/1986  Gould et al. .

Primary Examiner—V. Millin
Assistant Examiner—Perry E. Van Over
Attorney, Agent, or Firm—Joseph F. Breimayer

[57] ABSTRACT

A system for use in delivering a thrombolytic agent to a firm obstruction in a blood vessel by effecting longitudinal extension of the distal infusion segment of an infusion device through the obstruction as the obstruction is dissolved by the delivery of the thrombolytic agent. The infusion device is inserted into the lumen of an introducer to straighten the distal infusion segment and the assembly is advanced through a selected path in a patient's vascular system to the obstructed site. The distal infusion segment is advanced from a distal end opening of the introducer sheath lumen and assumes the pre-biased J-shaped bend configuration when positioned that tends to present the infusion port in a side wall toward the obstruction. A spring loaded assembly is coupled between the proximal ends of the infusion device and the introducer catheter that applies a force axially along the body of the infusion device against the resistance of the obstruction in contact with the distal infusion segment. As the dissolving agent is delivered and the obstruction dissolves, the distal infusion segment tunnels through the soft obstruction under the influence of the applied axial force.

18 Claims, 3 Drawing Sheets

LONGITUDINALLY EXTENDABLE INFUSION DEVICE

CROSS-REFERENCE TO RELATED APPLICATION

Reference is hereby made to commonly assigned, co-pending U.S. patent application Ser. No. 08/326,609 filed Oct. 20, 1994, for INFUSION DEVICE WITH PREFORMED SHAPE in the names of George B. Wallace, et al.

BACKGROUND OF THE INVENTION

1. Field of the Invention

The present invention relates to medical devices for use in delivering a thrombolytic agent to a firm obstruction in a blood vessel and particularly to such a device having a configuration and system for effecting longitudinal extension through the firm obstruction as the obstruction is dissolved by the delivery of the thrombolytic agent.

2. Description of the Background Art

The acute symptoms of blockage of a vein at a venous valve or a partially sclerosed and narrowed artery may be instigated by the presence of a soft obstruction or blood clot that is soft and jelly-like in consistency. Such blood clots may form for a variety of reasons in the vascular system and be released and flow until they block a partially occluded section of the blood vessel. When this clot blocks a vessel in the leg, for example, the resultant pain or loss of circulation requires its removal or dissolution.

Such soft obstructions are readily penetrated but reform after the penetrating object is removed. To effect the initial opening of a soft obstruction, thrombolytic drugs or clot dissolving agents may be applied through an infusion catheter inserted into the clot to encourage the dissolution of the clot. For example, the infusion catheter disclosed in U.S. Pat. No. 5,085,635 is proposed to be introduced over a guidewire previously advanced through the soft obstruction and be used for infusion of thrombolytic drugs (as well as diagnostic agents, in other procedures) out side wall openings into contact with the soft obstruction.

Some obstructions or blood clots are not "soft" and are not subject to easy penetration by a guidewire or convertible wire and consequently are characterized as "firm" obstructions. The typical treatment is to gain access to one end of the firm obstruction and to infuse the thrombolytic agent in proximity to that end to dissolve it. In the use of conventional infusion guidewires, convertible wires or catheters for introducing the dissolving agent in such a fashion, it is not always possible to direct a concentration of the dissolving agent into the firm obstruction, where the infused agent would provide the most benefit. Some of the infused thrombolytic agent has the desired effect while the majority of the agent flows away from the site.

It would be desirable to provide local delivery of dissolving agents to a firm obstruction or firm blood clot to magnify the therapeutic effects while minimizing the complications, e.g. bleeding, of systemically delivered thrombolytic agents. Similarly, it would be desirable to apply and concentrate such agents into the firm obstruction as it shrinks in response to the treatment. Despite the advances and improvements in treatment that have been introduced in recent years, a need remains for an infusion guidewire and catheter that provides a simple and less expensive way to assure delivery of drugs or agents into a firm obstruction to achieve its rapid dissolution and restoration of blood flow through the blood vessel.

One way to speed the penetration and dissolution of the firm obstruction would be to apply firm pressure against the accessed end thereof as the agent is infused. However, despite efforts to make the tips of catheters and infusion guidewires soft, the application of force to penetrate a firm obstruction is problematic since any mistake in positioning of the tip may cause it to penetrate through the vessel wall or tunnel sub-intimal passageways alongside the vessel lumen and to pass by the firm obstruction without treating it.

SUMMARY OF THE INVENTION

The term "obstruction" is employed in the remaining description of the preferred embodiments and in the claims to embrace and be the equivalent of a "firm obstruction" comprising a blood clot or embolus or thrombus that is not readily penetrable that is amenable to treatment in manner described hereafter. The term "dissolving agent" is intended to embrace thrombolytic agents or other drugs or agents for penetrating, loosening or dissolving such obstructions. The term "infusion device" embraces infusion catheters and infusion guidewires and the like.

It is therefore a principal object of the present invention to provide an infusion device that makes intimate, pressurized contact with and delivers drugs or agents for the dissolution of or otherwise treating such an obstruction in situ.

It is yet another object of the present invention to provide for the extension of the infusion segment through the obstruction as the obstruction being treated dissolves or opens up.

These and other objects of the invention are realized in an infusion device and method of use thereof comprising the steps of and means for introducing an elongated infusion device having an elongated body and internal lumen and a distal infusion segment through a patient's vascular system to the site of the obstruction, the infusion device having an infusion port in the distal infusion segment leading to the infusion lumen for infusing a dissolving agent in proximity with the obstruction, applying force axially along the body of the infusion device against the resistance of the obstruction, thereby storing potential energy in the infusion device, delivering the dissolving agent through the infusion device lumen and out of the infusion port and into the obstruction, and longitudinally extending the infusion device distally under the force of the potential energy as the resistance of the obstruction diminishes as it is dissolved.

More particularly, the infusion device and method of use thereof is configured for introduction through a selected path in a patient's vascular system to a site in a blood vessel adjacent to an obstruction to be treated and for infusing a dissolving agent into the obstruction and further comprises an elongated introducer catheter having an introducer catheter lumen and a distal end opening adapted to be introduced through a patient's vascular system to the site of an obstruction, an elongated infusion device having an infusion device body with a proximal end, an infusion device lumen and a distal infusion segment and adapted to be introduced through the introducer catheter lumen and extended distally of the distal end opening, the infusion device distal infusion segment having at least one infusion port formed therein in communication with the infusion device lumen for infusing a dissolving fluid introduced through the infusion device lumen; externally disposed force applying means for applying force axially along said infusion device body with respect to the introducer catheter to bias the distal infusion segment to extend distally from the introducer catheter and against the obstruction; and means for delivering the dissolving agent into the infusion device lumen and infusing it through the infusion port, whereby the applied force in the infusion device biases the distal infusion segment against the obstruction, and dissolution of the obstruction allows the distal infusion segment to be advanced distally and longitudinally extended through the obstruction.

Preferably, the infusion device is formed in the distal infusion segment with a pliant spring material in the side wall and with a bend so that the bend presents the side wall against the obstruction as it is advanced by the applied bias and the dissolution of the obstruction. Furthermore, the bend is preferably a J-shaped bend, and the distal infusion port(s) is formed in the bend region.

Preferably, one or more side wall infusion ports are provided in the distal infusion segment including the bend and the more proximal adjacent straight body section that are exposed as the distal infusion segment is advanced from the introducer catheter and into the obstruction.

The J-shaped bend in the distal infusion segment may be effected by a permanent deformation in the infusion device body that is straightened within the introducer catheter lumen for advancement to the site of the obstruction and assumes its shape on advancement out of the distal lumen opening.

In these alternative embodiments, the infusion device may also be used as a guidewire that is advanced to the obstruction site and the introducer catheter is advanced over it.

Advantageously, the invention may be used to remove blood clots by the chronic application of both force and dissolving agent directly against and into the clot without the danger of penetrating the blood vessel side wall and tunnelling into the intima and reduces the complications and expense attendant to the operative procedure.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
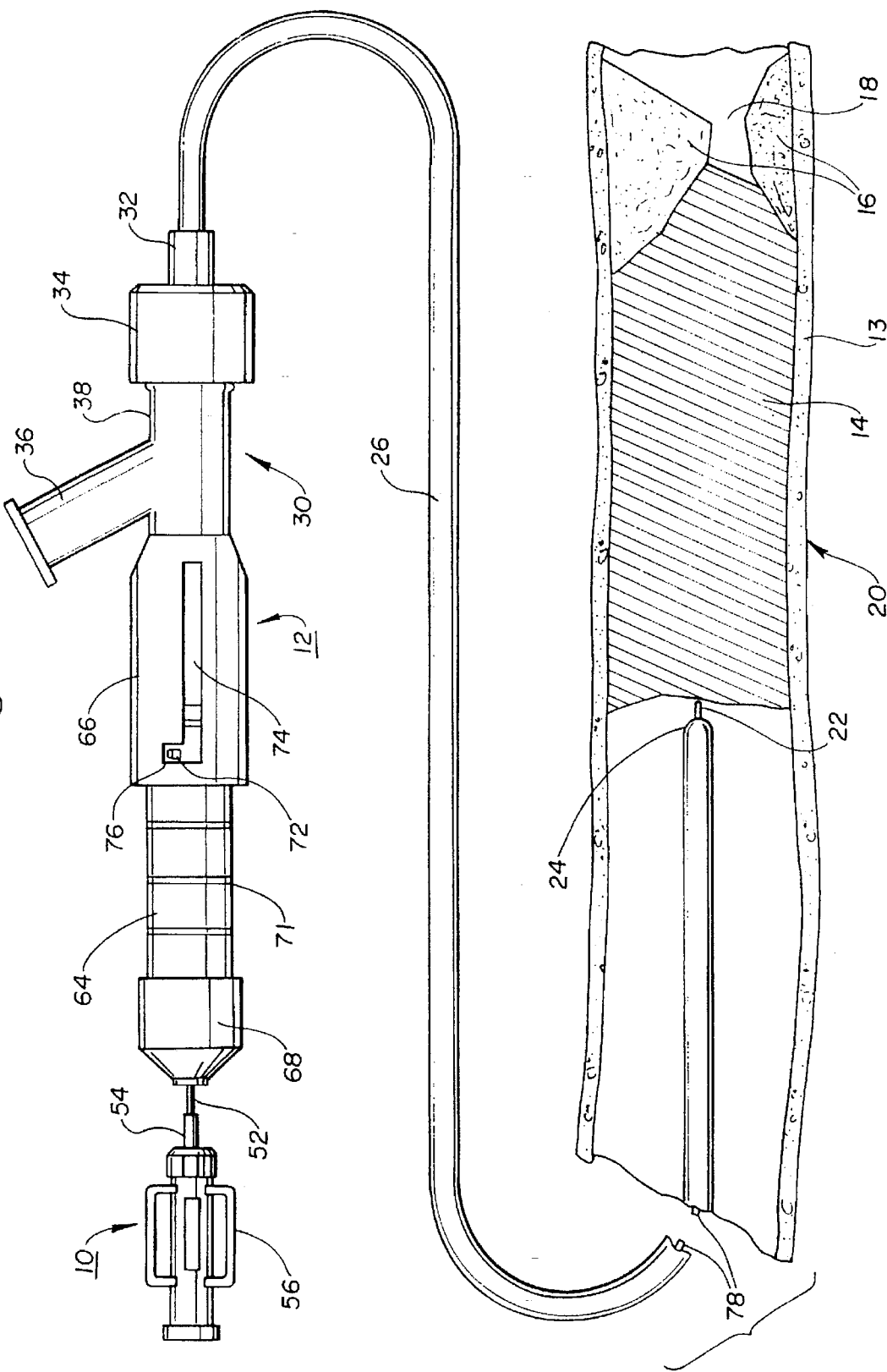
FIG. 1 is a plan view of the assembly of an infusion device and an introducer catheter inserted into a blood vessel in relation to an obstruction according to a preferred embodiment of the present invention.
Figure 2:
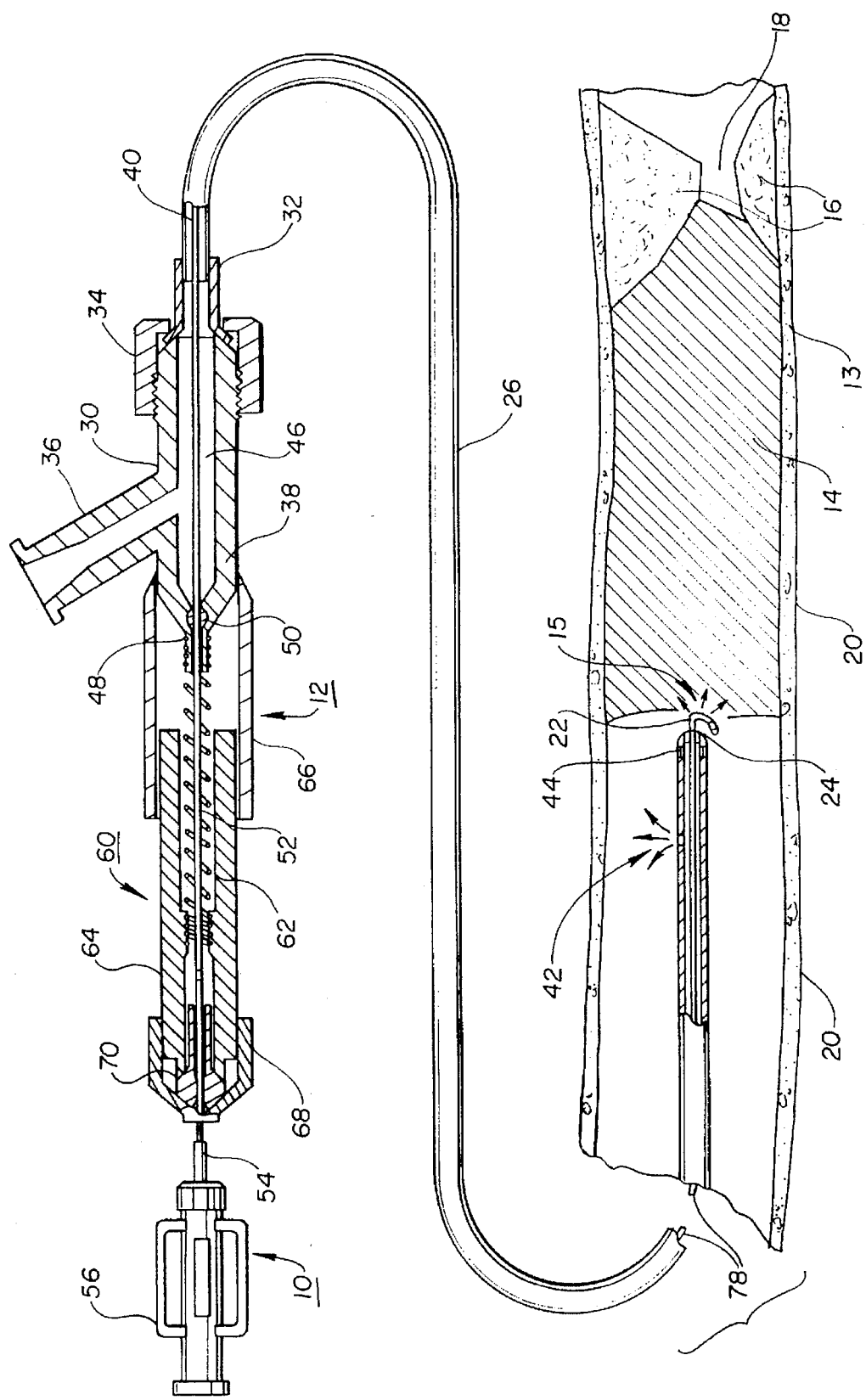
FIG. 2 is a partially sectioned view of the proximal end of the introducer catheter of FIG. 1 and also depicting the infusion device straightened within the introducer catheter lumen for introduction through a blood vessel in relation to an obstruction.

Turning first to FIGS. 1 and 2, they depict the assembly of an infusion device 10 and an introducer catheter 12 along in accordance with one preferred embodiment of the present invention in relation to an obstruction 14 in a blood vessel 20. The obstruction 14 is a firm blood clot that is lodged against a hard occlusion 16 or other constriction in the blood vessel 20 that leaves a constricted blood flow opening 18. The firm obstruction 14 blocks off the blood flow and causes symptoms to the patient that require its removal so that blood flow may be resumed through the constricted blood flow opening 18. The construction of a preferred embodiment of the infusion device 10 is depicted in FIGS. 3–6 and described below.

In FIG. 1, the distal infusion segment 22 is shown straightened and within the introducer sheath lumen 40. Preferably, the distal end of introducer sheath 26 includes a ring shaped, radiopaque marker 44 formed in the sidewall thereof and a penetrable flap valve structure that seals the introducer sheath end opening 24 but allows the distal infusion segment 22 to be advanced through it in the manner disclosed in U.S. Pat. No. 5,085,635, to Cragg, incorporated herein by reference.

In FIG. 2, the distal infusion segment 22 of infusion device 10 is shown emerging from the distal end opening 24 of the elongated introducer lumen within the elongated introducer sheath 26. As described below, a bias force is effected down the length of the infusion device body to bias the J-shaped distal infusion segment 22 against the obstruction 14. A dissolving agent is applied from a source attached to luer hub assembly 56 and emitted from infusion ports in the J-shaped distal infusion segment 22. As the obstruction 14 is dissolved, the biasing force advances it distally out of the introducer sheath distal end opening 24 and through the obstruction 14.

As shown in FIGS. 1 and 2, an introducer Y-fitting 30 is attached to the proximal end of the introducer sheath 26 through a strain relief 32 and a compression cap 34. A side branch 36 extends off from the trunk 38 of the Y-fitting 30 in fluid communication with the Y-fitting conduit 46 which is in fluid communication with the introducer sheath lumen 40. The side branch 36 is adapted to be attached to a supply for thrombolytic agents for transmission through the introducer sheath lumen 40 alongside the infusion device 10 and emission through the sidewall exit port(s) 42 formed in the sidewall of the introducer sheath 26. The penetrable flap valve structure seals the introducer sheath end opening 24 around the distal infusion segment 22 advanced through it while the thrombolytic agent is emitted through the side hole exit port(s) 42.

As described below with respect to FIGS. 3–6, an exposed proximal end segment 52 of the elongated tubular body of infusion device 10 is preferably formed of a length of metal hypotube terminating proximally in strain relief 54 and a luer hub assembly 56 and extending distally within an exterior infusion sheath 78. The Y-fitting trunk 38 extends proximally to a fitting proximal stem 48 having a dynamic seal 50 formed therein, e.g. a trapped lubricated O-ring, through which the length of exposed hypotube in proximal end segment 52 slidably extends proximally.

From fitting proximal stem 48, the length of hypotube 52 also extends proximally through a tensioning or biasing assembly 60 to its termination within the luer hub assembly 56. The biasing assembly 60 includes a biasing coil spring 62, telescoping inner housing 64, outer housing 66 and housing end cap 68. The inner housing 64 rotatably engages the outer housing 66, and a distal end of biasing spring 62 is fitted over the fitting proximal stem 48 within outer housing 66. The inner housing 64 and the proximal end of biasing coil spring 62 are attached together at a point distal to housing end cap 68. As shown in FIG. 2, the housing end cap 68 is threaded over the proximal end of the inner housing 64. The housing cap 68 encloses a compressible ring collet 70 that tightly engages the hypotube 52 when the cap 68 is tightly screwed to the inner housing 64 so that the proximal end of biasing spring 62 is fixed to the hypotube 52 in proximal end segment 52.

The inner housing 64 is provided with a series of visible distance markers 71 that show the distance that the distal infusion segment 22 is advanced against the resistance of the obstruction 14. In the assembly of the infusion device 10 and introducer catheter 12 as shown in FIGS. 1 and 2, the biasing spring 62 is initially stretched axially a maximal amount to develop the biasing force that tends to draw the distal end of outer housing 66 and the housing end cap 68 toward one another and to advance the distal infusion segment 22 from the distal end opening 24 of the introducer catheter 12.

A releasable locking mechanism is provided in order to maintain the coil spring 62 stretched and the distal infusion segment 22 within the introducer sheath lumen 40. A locking pin 72 extends outward from inner housing 64 and through an elongated guide slot 74 in outer housing 66 and engages in a circumferential leg 76 in the locked position as shown in FIG. 1. The J-shaped bend in the distal infusion segment 22 is thereby straightened and maintained within the introducer lumen 40 during the intravascular introduction of the infusion device 10 and the introducer catheter 12 to the site of the obstruction 14. The locking mechanism is released in FIG. 2, and the distal infusion segment 22 is advanced to form the unrestrained blunt bend.

In clinical use, after the distal end opening of the introducer catheter is placed at the obstruction site, the Y-fitting trunk 38 is taped to the patient adjacent to the puncture made to introduce the introducer catheter 12 and infusion device 10 into the patient's vascular system. Then, the inner housing 64 is rotated to the released position, allowing the guide pin 72 to travel in the elongated guide slot 74. The biasing force is overcome, however, by the obstruction 14. The dissolving agent is then infused from the distal infusion segment 22 and begins to dissolve away the obstruction 14 creating the pocket 15 shown in FIG. 2. As the distal infusion segment 22 advances distally under the force applied by the biasing spring 62, the pocket 15 forms into a tunnel to the constricted blood flow opening 18. As the distal infusion segment 22 advances, the inner housing 64 is drawn into the outer housing 66, and the visible markers 71 provide an easily interpreted indication of the amount of advancement that has taken place.

Normally, the obstruction 14 is not uniformly firm through out its length, and once pocket 15 is formed, the penetration under the spring bias force is relatively quick to the maximum travel of the inner and outer housings 64 and 66. On observing the change in the markers 71, the attending staff may be able to manually advance the infusion device through the remaining, less firm length of the obstruction. If necessary, the amount of advancement under the bias force can be increased by engaging the locking mechanism to stretch the spring 62, resetting the point of engagement along the length of the hypotube in proximal end segment 52 by the compressible ring collet 70 and housing end cap 68, and again releasing the locking mechanism. Additional visible distance markings may be provided along the length of the hypotube in proximal end segment 52 for gauging advancement distances.

A syringe or other pump system may be sealingly coupled to the proximal end of infusion device 10 by the standard luer hub assembly 56 or a Touhy-Borst connector or any other connector. In the preferred mode, and not to be deemed as limiting of the invention, the dissolving agent is delivered by an infusion pump attached to luer hub assembly 56.

Figure 6:
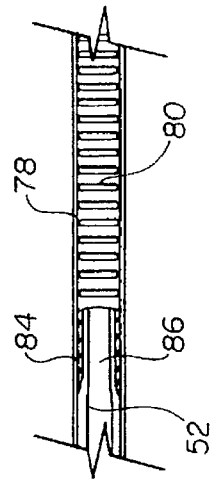
FIG. 6 is a partial cross-section view of an intermediate segment of the infusion device of FIGS. 3 and 4.

Turning now to FIGS. 3–6, the infusion device is depicted in greater detail. Preferably, the infusion device 10 is formed of an elongated tubular body constructed of an exterior infusion sheath 78, preferably formed of a Teflon® PTFE heat shrink tube, and interior structure forming a proximal section and a distal section. The interior structure of the proximal section comprises the hypotube 52, and the interior structure of the distal section includes rectangular cross-section, pliant metal wire coil 80 with spaced apart turns. Both the hypotube 52 and the wire coil 80 and the junction 82 of the hypotube 52 with the wire coil 80 are encased within the exterior infusion sheath 78. The infusion lumen 86 is formed within the hypotube 52 and the turns of wire coil 80 inside exterior infusion sheath 78 and extends proximally to the luer hub assembly 56. FIG. 6 depicts the junction 82 in detail and shows the swaged down distal end 84 of hypotube 52 with the proximal end of the wire coil 80 fitted over it and brazed to it.

Figure 3:
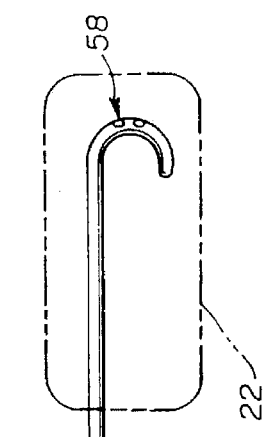
FIG. 3 is a plan view of the infusion device of FIGS. 1 and 2.
Figure 4:
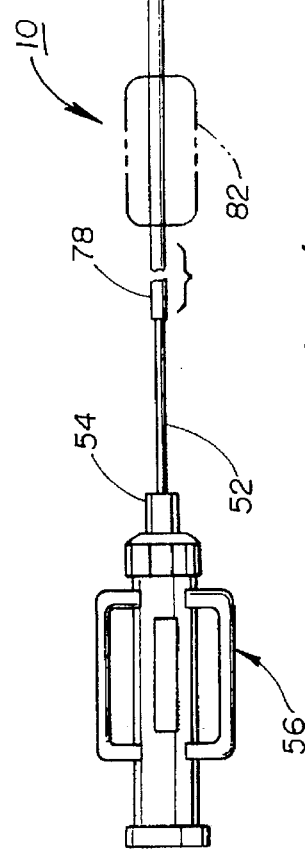
FIG. 4 is an end view of the infusion device of FIG. 3.
Figure 4:
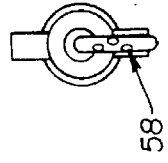
Figure 5:
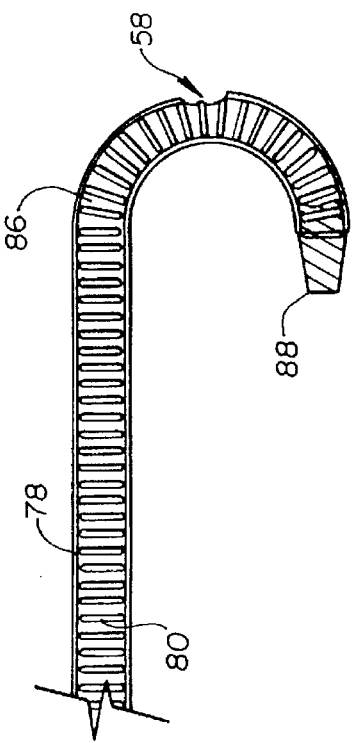
FIG. 5 is a partial cross-section view of the J-shaped distal infusion segment of the infusion device of FIGS. 3 and 4.

Turning to the distal infusion segment 22, the distal end of the distal infusion lumen 86 is closed by a distal plug 88 shown in FIG. 5. One or more distal infusion side holes or ports 58 extending from the infusion lumen 86 through the side wall comprised of the outer exterior infusion sheath 78 and the wire coil 80 are depicted in FIGS. 3, 4 and 6. The J-shaped bend is formed in the distal infusion segment 22 so that the bend presents the infusion device side wall with the infusion ports 58 formed therein against the obstruction 14 as the distal infusion segment 22 is advanced by the applied bias and the dissolution of the obstruction 14.

Preferably, a plurality of side hole infusion ports 58 are provided in the distal infusion segment including the bend and the more proximal adjacent straight body section that are exposed as the distal infusion segment 22 is advanced from the introducer catheter 12 and into the obstruction 14.

The J-shaped bend in the distal infusion segment 22 may be effected by a permanent deformation in the infusion device body and straightened within the introducer catheter lumen for advancement to the site of the obstruction 14. Alternatively, the distal infusion segment may be normally straight and deflectable into the J-shaped bend under the influence of a pull wire, or it may be formed with a temperature dependent shape memory metal element that assumes the J-shape in situ upon reaching body temperature. In the latter case, the side walls of the infusion device body assume a straight shape within the introducer catheter lumen at a temperature less than body temperature that may be maintained by infusion of a cooling fluid to allow the introducer catheter and infusion device to be introduced together to the obstruction site. The advancement of the distal infusion segment from the introducer catheter lumen heats the temperature dependent element which curves into the J-shape.

The introducer catheter 12 may be of any of the known types and may be first introduced to the obstruction site with or without the infusion device 10 inside the introducer sheath lumen 40. The infusion device 10 may alternatively be used as an infusion guidewire or "convertible wire" with a removable core wire extended down the infusion lumen 86 to straighten it. The luer hub assembly 56 can be removed from the proximal end of the hypotube 52 to allow the infusion device 10 to function as an ordinary guidewire using the removable core wire. When the obstruction 14 is reached, the introducer catheter 12 may then be advanced to the positions depicted in FIGS. 1 and 2, and the core wire may be removed so that infusion may take place as described above.

In either case, the tensioning or biasing assembly 60 of the introducer catheter 12 provides the function of applying the differential biasing force to the infusion hypotube 52 which slips distally through the dynamic seal 50 as the J-shaped bend in the distal infusion segment 22 advances through the dissolved tunnel formed in the obstruction 14.

In the case where the distal infusion segment is formed with a memory metal, e.g. a Ni-Ti alloy that assumes the J-shaped bend configuration at an elevated temperature. The memory metal may be used to form the J-shaped bend at a transition temperature that may, for example, be body temperature. In such a case, the elevation of the temperature of the distal infusion segment 22 from room to body temperature effects the change from straight to coiled configuration upon advancement form the distal introducer sheath opening 24. The temperature of the wire may also be elevated by the use of other energy sources such as by passing an electrical current through the wire. It will be understood that a cooling fluid, e.g. cooled saline, may be infused down the introducer sheath lumen 40 and/or infusion lumen 86 during introduction of the infusion device to keep the distal infusion segment 22 straight until the obstruction 14 is reached.

The J-shaped bend in the distal infusion segment 22 operates to effectively blunt the tip of the infusion device 10 and to decrease the possibility of damage to the blood vessel wall 13. Any other suitable shape may be substituted for the J-shape to effect the blunting of the tip.

The wire coil 80 of infusion device 10 may be constructed by any of the known methods in monofilar and in multi-filar coiled wire windings and in one or more coaxial coils of circular or rectangular cross-section wire around an inner lumen in a manner shown in the prior art. In any of the depicted embodiments, wire coil 80 is preferably a spring coil of stainless steel wire which is wound with a constant or variable pitch.

Although the preferred embodiments depict a single, distal, infusion segment 22, it will also be understood that more than one such infusion segment as described above may be formed along the length of the infusion device body. Moreover, it will be understood that the distal infusion segment as described above in its various embodiments refers to any such infusion segment located anywhere along the length of the infusion device body distal to the proximal end thereof and not necessarily at the location generally depicted in the figures.

Although a stretched extension spring is disclosed coaxially surrounding the proximal end section of the infusion device in the preferred embodiments to provide the biasing force, it will be understood that other types of springs, e.g. a constant force spring, and other spring loading mechanisms may be provided in substitution therefore.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

PARTS LIST FOR FIGS. 1–6 infusion device 10
introducer catheter 12
blood vessel wall 13
obstruction 14
pocket 15
hard occlusion 16
constricted blood flow opening 18
blood vessel 20
distal infusion segment 22
introducer sheath distal end opening 24
elongated introducer sheath 26
introducer Y-fitting 30
strain relief 32
compression cap 34
Y-fitting side branch 36
Y-fitting trunk 38
introducer sheath lumen 40
sidewall exit port 42
radiopaque marker 44
Y-fitting conduit 46
fitting proximal stem 48
dynamic seal 50
proximal end segment 52
strain relief 54
luer hub assembly 56
infusion ports 58
tensioning or biasing assembly 60
biasing coil spring 62
telescoping inner housing 64
outer housing 66
housing cap 68
compressible ring collet 70
locking pin 72
elongated guide slot 74
circumferential leg 76
exterior infusion sheath 78
wire coil 80
junction 82
swaged down distal end 84
infusion lumen 86
distal plug 88

What is claimed is:

1. An infusion system for applying pressure against a firm obstruction in a blood vessel while infusing a drug or agent for dissolving the firm obstruction comprising:

an elongated infusion device having an elongated tubular body extending between a proximal end and a distal end thereof containing an internal infusion lumen and adapted to be advanced through a patient's vascular system until the distal end is located in proximity to the site of the obstruction, the elongated tubular body having at least one infusion port in a distal infusion segment thereof adjacent said distal end in fluid communication with the infusion lumen for infusing a dissolving agent in proximity to the obstruction, and proximal end hub means coupled to said proximal end of said elongated body for attachment to a source of dissolving agent for delivering the dissolving agent through the infusion device lumen and out of the infusion port and into the obstruction;

means for applying force axially along the elongated tubular body of the infusion device against the resistance of the obstruction in contact with the distal infusion segment, thereby storing potential energy in the infusion device;

means for longitudinally extending the infusion device distally under the force of the potential energy as the resistance of the obstruction to said force diminishes as it is dissolved.

2. The infusion system of claim 1 wherein said elongated tubular body is pre-biased to form an expanded blunt infusion configuration in said distal infusion segment to provide an increased contact surface in contact with said obstruction to thereby blunt the distal end of said elongated body.

3. The infusion system of claim 2 wherein:

said infusion configuration comprises a J-shaped bend and said infusion port is formed as an opening in the infusion sheath around the outside of the J-shaped bend for allowing infusion directly in the area of contact with the obstruction and diminishing the possibility of penetrating the vessel wall.

4. The infusion device of claim 3 wherein said elongated tubular body further comprises:

an elongated wire coil having spaced coil turns surrounding a portion of said infusion lumen extending from said distal end through said distal infusion segment; and an elongated exterior infusion sheath extending from said proximal end to said distal end of said elongated tubular body for encasing said elongated wire coil and sealing said infusion lumen; and wherein:

each said infusion port is formed as an opening in said infusion sheath in said distal infusion segment for allowing passage of said infusion fluid from said infusion lumen between said spaced coil wire turns and through said opening.

5. The infusion device of claim 1 wherein said elongated tubular body further comprises:

an elongated wire coil having spaced coil turns surrounding a portion of said infusion lumen extending from said distal end through said distal infusion segment; and an elongated exterior infusion sheath extending from said proximal end to said distal end of said elongated tubular body for encasing said elongated wire coil and sealing said infusion lumen; and wherein:

each said infusion port is formed as an opening in said infusion sheath in said distal infusion segment for allowing passage of said infusion fluid from said infusion lumen between said spaced coil wire turns and through said opening.

6. The infusion system of claim 1 wherein said longitudinally extending means further comprises:

an introducer catheter of the type having an elongated, tubular introducer sheath extending between a an introducer sheath proximal end and an introducer sheath distal end and having an introducer sheath lumen formed therein extending from said introducer sheath proximal end to a distal end opening at said introducer sheath distal end; and proximal end fitting means coupled to said introducer sheath proximal end having a tubular conduit therein aligned with said introducer sheath lumen for receiving a proximal end segment of said infusion device therein and for facilitating the advancement of said infusion device distally through said introducer sheath lumen and said distal infusion segment out said introducer sheath distal end opening such that said distal infusion segment is biased against said firm obstruction.

7. The infusion system of claim 6 wherein said force applying means further comprises:

means coupled between said proximal end fitting and said proximal end hub means of said infusion device for applying biasing force axially and distally along said infusion device with respect to said introducer sheath and for biasing said infusion device distal end against said firm obstruction.

8. The infusion system of claim 7 wherein said elongated tubular body is pre-biased to form an expanded blunt infusion configuration in said distal infusion segment to provide an increased contact surface in contact with said obstruction to thereby blunt the distal end of said elongated body.

9. The infusion system of claim 8 wherein:

said infusion configuration comprises a J-shaped bend and said infusion port is formed as an opening in the infusion sheath around the outside of the J-shaped bend for allowing infusion directly in the area of contact with the obstruction and diminishing the possibility of penetrating the vessel wall.

10. The infusion device of claim 9 wherein said elongated tubular body further comprises:

an elongated wire coil having spaced coil turns surrounding a portion of said infusion lumen extending from said distal end through said distal infusion segment; and an elongated exterior infusion sheath extending from said proximal end to said distal end of said elongated tubular body for encasing said elongated wire coil and sealing said infusion lumen; and wherein:

each said infusion port is formed as an opening in said infusion sheath in said distal infusion segment for allowing passage of said infusion fluid from said infusion lumen between said spaced coil wire turns and through said opening.

11. The infusion system of claim 6 wherein said elongated body is pre-biased to form an expanded bend infusion configuration in said distal infusion segment to provide an increased contact surface in contact with said obstruction to thereby blunt the distal end of said elongated body.

12. The infusion system of claim 11 wherein:

said infusion configuration comprises a J-shaped bend and said infusion port is formed as an opening in the infusion sheath around the outside of the J-shaped bend for allowing infusion directly in the area of contact with the obstruction and diminishing the possibility of penetrating the vessel wall.

13. The infusion device of claim 12 wherein said elongated tubular body further comprises:

an elongated wire coil having spaced coil turns surrounding a portion of said infusion lumen extending from said distal end through said distal infusion segment; and an elongated exterior infusion sheath extending from said proximal end to said distal end of said elongated tubular body for encasing said elongated wire coil and sealing said infusion lumen; and wherein:

each said infusion port is formed as an opening in said infusion sheath in said distal infusion segment for allowing passage of said infusion fluid from said infusion lumen between said spaced coil wire turns and through said opening.

14. A method for introducing a drug or agent into a patient's vascular system to dissolve a firm obstruction therein comprising the steps of:

providing an elongated tubular body of an infusion device extending between a proximal and a distal end thereof having at least one infusion lumen formed therein extending from the proximal end to at least one distal infusion port;

forming a distal infusion segment adjacent said distal end of the elongated tubular body to assume an expanded bend infusion configuration in said distal infusion segment to provide an increased contact surface in contact with said obstruction to thereby blunt the distal end of said elongated body and that tends to position the infusion port distally and toward an obstruction in a blood vessel;

positioning the distal infusion segment adjacent to a firm obstruction in a blood vessel in the expanded bend configuration;

applying force axially along the elongated tubular body of the infusion device against the resistance of the obstruction in contact with the distal infusion segment, thereby storing potential energy in the infusion device;

delivering the dissolving agent to said proximal end hub means, through the infusion device lumen and out of the infusion port and into the obstruction; and longitudinally extending the infusion device distally under the force of the potential energy as the resistance of the obstruction diminishes as it is dissolved.

15. The method of claim 14 wherein:

said forming step further comprises forming a J-shaped bend in said distal infusion segment when positioned in a blood vessel with said at least one distal infusion port in the outer surface of the J-shaped bend adapted to be positioned distally and toward an obstruction in a blood vessel; and said positioning step further comprises positioning the distal infusion segment adjacent to a firm obstruction in a blood vessel in the J-shaped bend configuration.

16. The method of claim 15 wherein said positioning step further comprises:

straightening the J-shaped bend in the distal infusion segment within an introducer sheath lumen of an introducer catheter for facilitating advancement of both the distal infusion segment and the distal end opening of the introducer catheter to a selected location in a blood vessel;

advancing said introducer catheter and said infusion device with said restrained distal infusion segment through the patient's vascular system to locate said distal infusion segment at a desired site in a blood vessel;

advancing said distal infusion segment out of said distal end opening of said introducer sheath lumen and allowing said distal infusion segment to assume said J-shaped bend infusion configuration.

17. The method of claim 16 wherein said force applying step further comprises:

stabilizing the proximal end of said introducer catheter with respect to the patient;

applying a force between the proximal end of said introducer catheter and the proximal end of said infusion device and axially along the body of the infusion device against the resistance of the obstruction in contact with the distal infusion segment.

18. The method of claim 15 wherein said positioning step further comprises:

straightening the J-shaped bend in the distal infusion segment for facilitating advancement of said distal infusion segment to a selected location in a blood vessel;

advancing said infusion device with said restrained distal infusion segment through the patient's vascular system to locate said distal infusion segment at a desired site in a blood vessel; and allowing said distal infusion segment to assume said J-shaped bend infusion configuration.

* * * * *